United States Patent [19]
Kaplan et al.

[11] Patent Number: 5,855,563
[45] Date of Patent: *Jan. 5, 1999

[54] METHOD AND APPARATUS FOR SEQUENTIALLY PERFORMING MULTIPLE INTRALUMINAL PROCEDURES

[75] Inventors: Aaron V. Kaplan, Los Altos; James R. Kermode, Sunnyvale; Enrique J. Klein, Los Altos, all of Calif.

[73] Assignee: Localmed, Inc., Palo Alto, Calif.

[*] Notice: This patent issued on a continued prosecution application filed under 37 CFR 1.53(d), and is subject to the twenty year patent term provisions of 35 U.S.C. 154(a)(2).

[21] Appl. No.: 666,778

[22] Filed: Jun. 19, 1996

Related U.S. Application Data

[60] Division of Ser. No. 222,143, Apr. 1, 1994, Pat. No. 5,571,086, which is a continuation-in-part of Ser. No. 47,737, Apr. 15, 1993, Pat. No. 5,336,178, which is a continuation-in-part of Ser. No. 969,595, Nov. 2, 1992, abandoned.

[51] Int. Cl.⁶ .................................................. A61M 31/00
[52] U.S. Cl. .............................. 604/49; 604/96; 604/104; 604/105; 600/439; 600/447; 600/462; 600/467
[58] Field of Search ..................... 604/96, 101, 104–105, 604/52, 49; 606/192, 194; 128/660.01, 660.03, 660.07, 661.01, 662.06; 600/437, 439, 443, 447, 462, 466, 467

[56] References Cited

U.S. PATENT DOCUMENTS

| | | | |
|---|---|---|---|
| 3,938,502 | 2/1976 | Bom | 128/2 |
| 4,576,177 | 3/1986 | Webster, Jr. | 128/660 |
| 4,661,094 | 4/1987 | Simpson | 604/53 |
| 4,776,337 | 10/1988 | Pakmaz | 128/343 |
| 4,841,977 | 6/1989 | Griffith et al. | 128/660 |
| 4,911,163 | 3/1990 | Fina | 606/127 |
| 4,917,097 | 4/1990 | Proudian et al. | 128/662 |
| 4,976,689 | 12/1990 | Buchbinder et al. | 604/95 |
| 5,009,636 | 4/1991 | Wortley et al. | 604/43 |
| 5,087,247 | 2/1992 | Horn et al. | 604/98 |
| 5,092,877 | 3/1992 | Pinchuck | 623/1 |
| 5,102,390 | 4/1992 | Crittenden et al. | 604/96 |
| 5,102,415 | 4/1992 | Guenther et al. | 606/159 |
| 5,117,831 | 6/1992 | Jang et al. | 128/662 |
| 5,163,921 | 11/1992 | Feiring | 604/247 |
| 5,180,364 | 1/1993 | Ginsburg | 604/53 |
| 5,192,307 | 3/1993 | Wall | 623/1 |
| 5,203,338 | 4/1993 | Jang | 128/662 |
| 5,219,335 | 6/1993 | Willard et al. | 604/164 |
| 5,242,451 | 9/1993 | Harada et al. | 606/108 |
| 5,254,089 | 10/1993 | Wang | 604/96 |
| 5,266,073 | 11/1993 | Wall | 62/1 |
| 5,281,200 | 1/1994 | Corso, Jr. et al. | 604/96 |
| 5,411,507 | 5/1995 | Heckele | 606/108 |

OTHER PUBLICATIONS

Bom, et al. (1989) "Early and Recent Intraluminal Ultrasound Devices" *International Journal of Cardiac Imaging* 4:79–88.

EndoSonics, the Cathscanner® Intracoronary Imaging System, A Step Beyond Intravascular Ultrasound.

*Primary Examiner*—Wynn Wood Coggins
*Assistant Examiner*—Cris L. Rodriguez
*Attorney, Agent, or Firm*—Townsend and Townsend and Crew LLP

[57] ABSTRACT

Sleeve catheters having an interactive device near their distal ends are provided for introduction while disposed over conventional interventional and imaging catheters. Exemplary interactive devices on the sleeve catheters include ultrasonic imaging arrays, drug delivery lumens, and the like. The sleeve catheters are most commonly used with angioplasty catheters, stent placement catheters, atherectomy catheters, and the like.

31 Claims, 11 Drawing Sheets

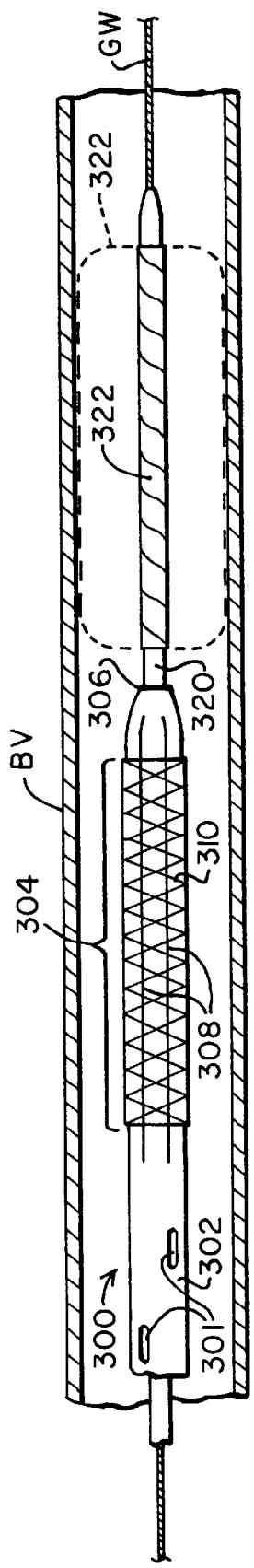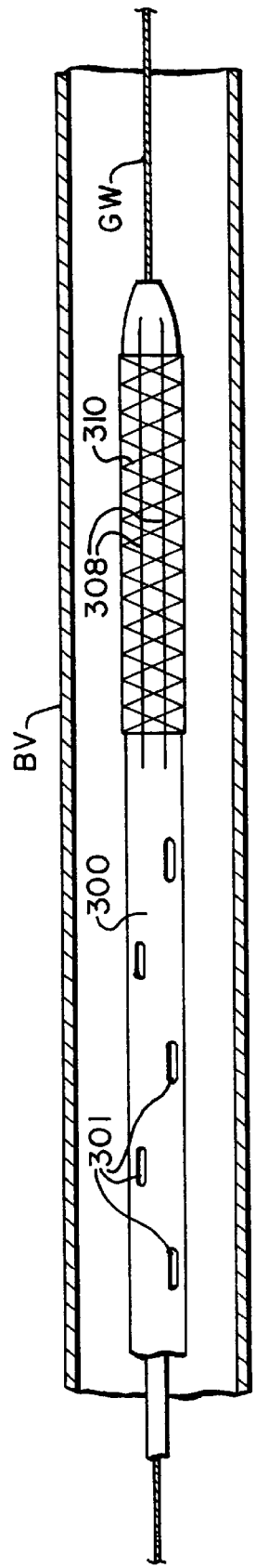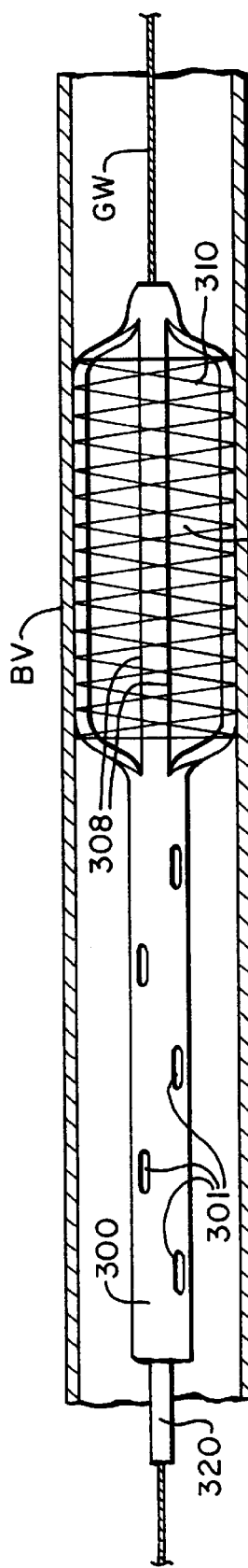

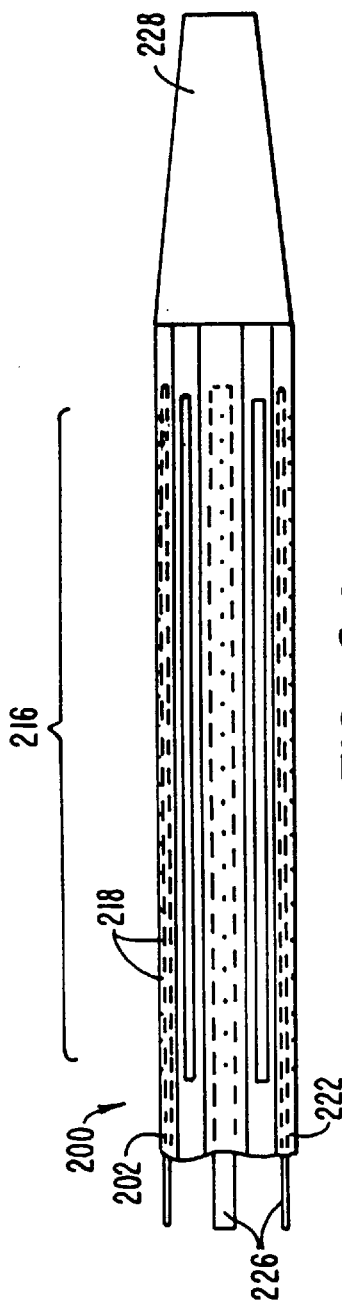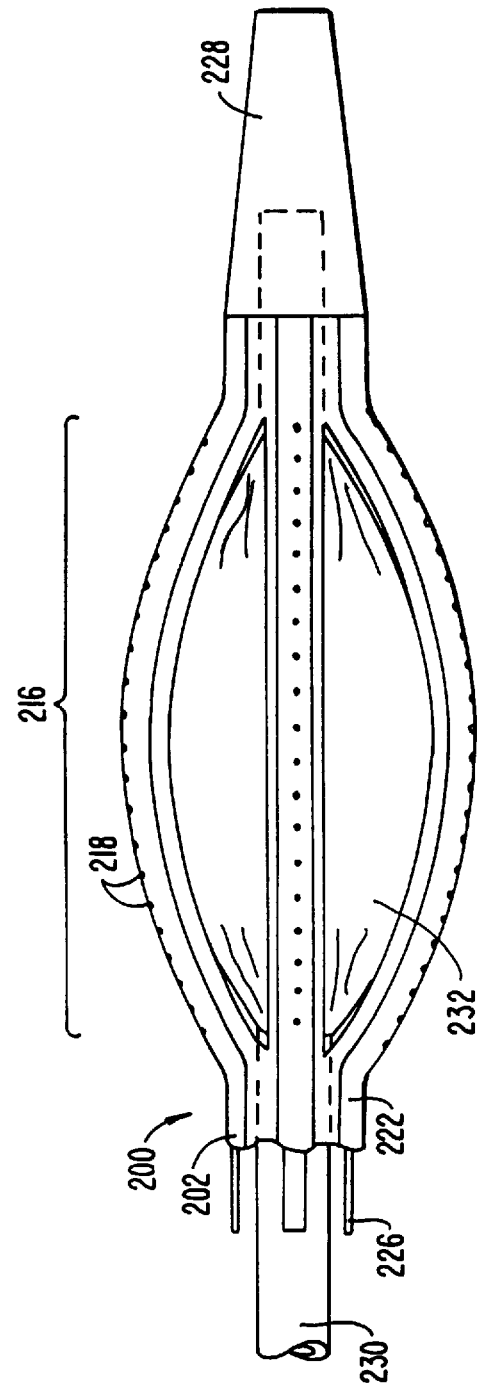

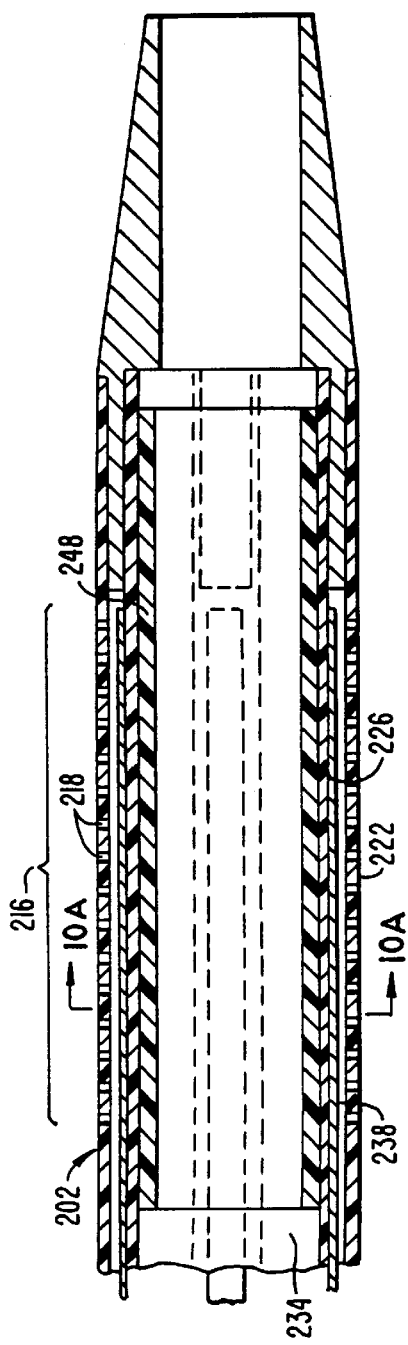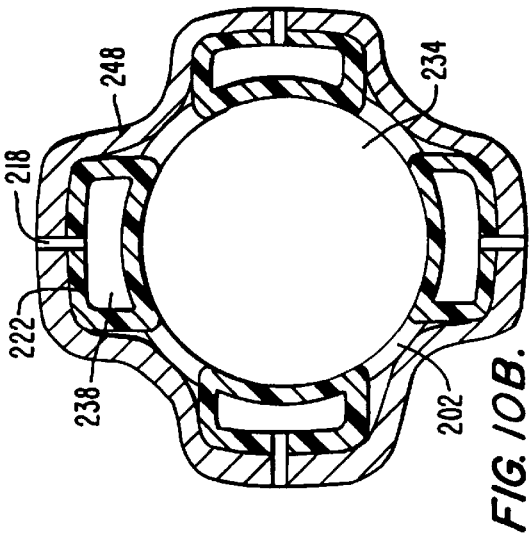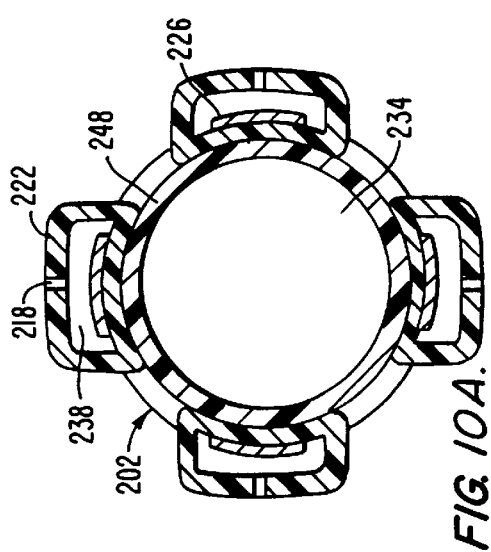

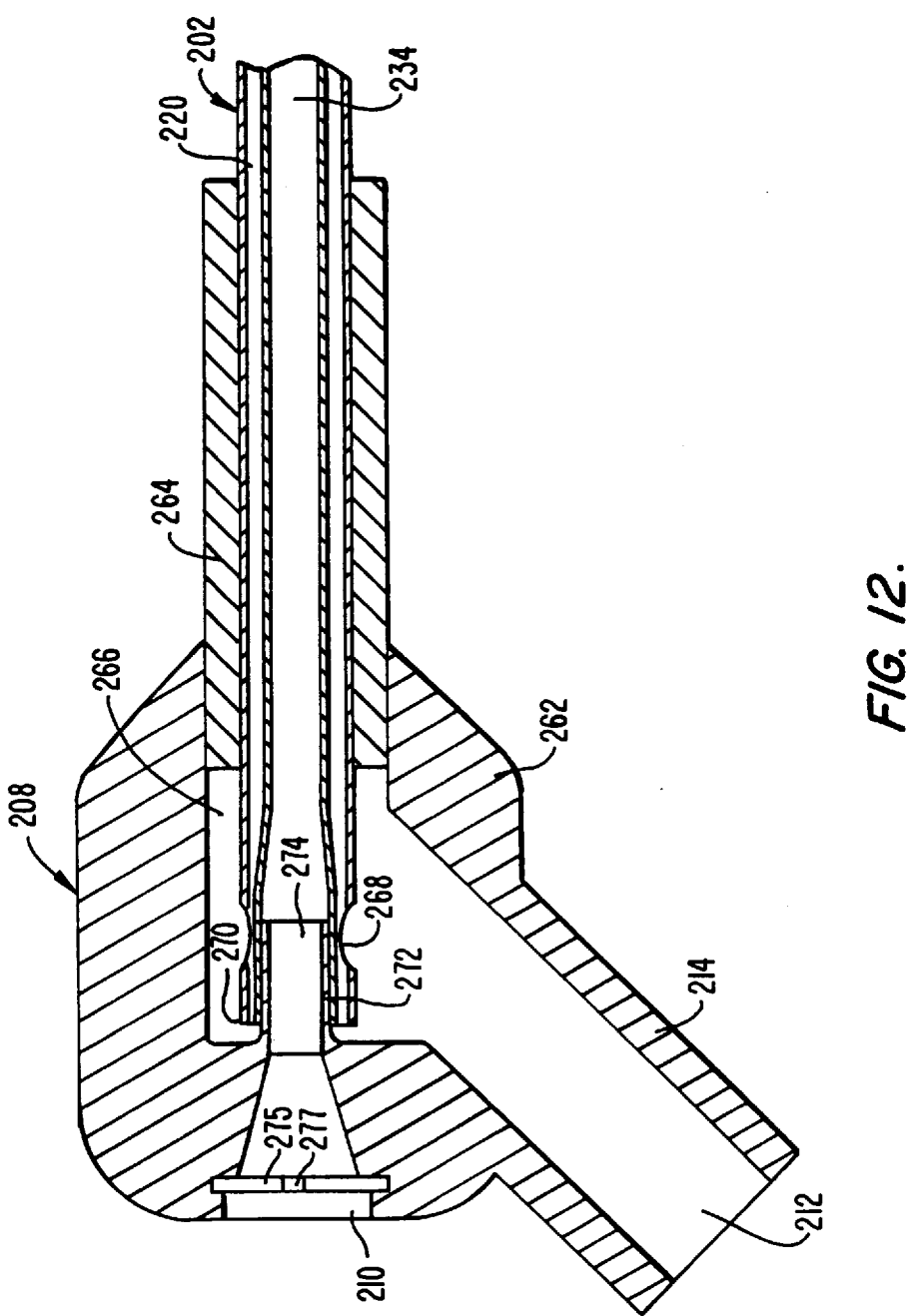

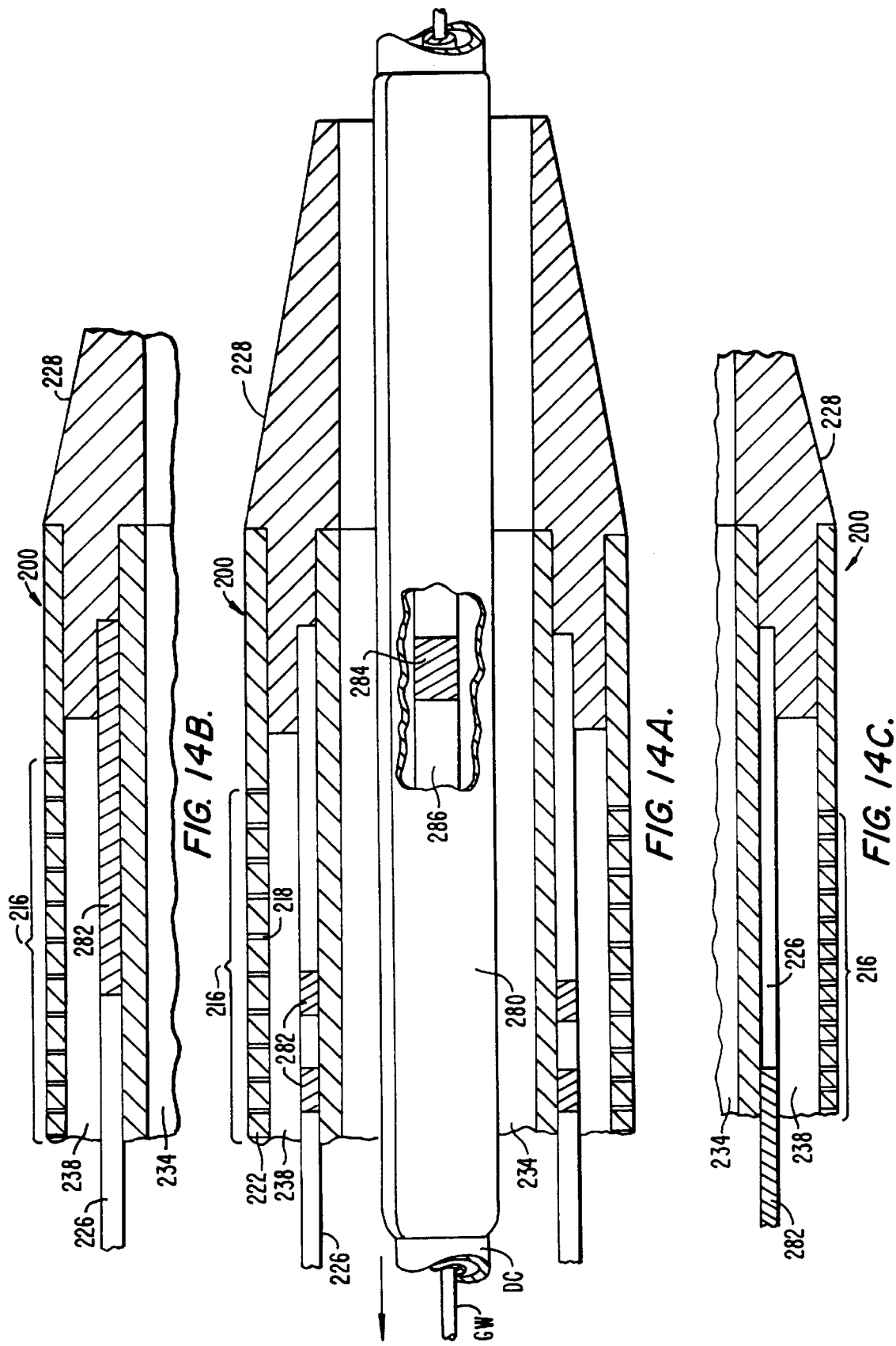

METHOD AND APPARATUS FOR SEQUENTIALLY PERFORMING MULTIPLE INTRALUMINAL PROCEDURES

This is a Division of application Ser. No. 08/222,143, filed Apr. 1, 1994, now U.S. Pat. No. 5,571,086, which was a Continuation-in-Part of application Ser. No. 08/047,737, filed Apr. 15, 1993 now U.S. Pat. No. 5,336,178, which was a Continuation-in-Part of application Ser. No. 07/969,595, filed Nov. 2, 1992, now abandoned.

BACKGROUND OF THE INVENTION

The present application is also related to application Ser. No. 08/221,613 (Attorney Docket No. 15509-7), filed simultaneously herewith, the complete disclosure of which is incorporated herein by reference.

1. Field of the Invention

The present invention relates generally to methods and devices for performing multiple, sequential intraluminal procedures. In particular, the method and apparatus utilize two or more interactive devices, including therapeutic and diagnostic devices, on separate catheters by selectively positioning at least one of the devices at a desired target site within the lumen while the other device(s) remain close by for subsequent use.

In percutaneous transluminal angioplasty procedures, a catheter having an expandable distal end, usually in the form of a balloon, is positioned in a lumen of a blood vessel with the distal end disposed within a stenotic atherosclerotic region of the vessel. The expandable end is then expanded to dilate the vessel and, upon withdrawal, restores adequate blood flow through the diseased region. During dilatation, blood flow is interrupted, limiting inflation time to between 0.5 and 3 minutes.

While angioplasty has gained wide acceptance, it continues to be limited by two major problems, abrupt closure and restenosis. Abrupt closure refers to the acute occlusion of a vessel immediately after or within the initial hours following the dilatation procedure. This complication occurs in approximately one of twenty cases and frequently results in myocardial infarction and death if blood flow is not quickly restored. At present, arterial dissections are treated by prolonged balloon inflations lasting more than 5 minutes. Special angioplasty balloon catheters which allow for perfusion through the dilatation catheter during inflation are usually necessary for such prolonged procedure.

Restenosis refers to the re-narrowing of an artery after an initially successful angioplasty. Occurring usually within the initial six months after angioplasty, restenosis afflicts approximately one in three cases. That is, approximately one in three patients will require additional revascularization procedures. Many different strategies have been tried unsuccessfully to reduce the restenosis rate, including mechanical (e.g., prolonged balloon inflations, atherectomy, laser and stenting) and pharmacologic (e.g., calcium antagonists, ace inhibitors, fish oils, steroids and anti-metabolic) approaches. A promising new strategy is to deliver agent directly to the arterial wall at the site of angioplasty. Several devices have been developed to deliver agent locally into the arterial wall. Similar to angioplasty balloon catheters, most drug delivery catheters interrupt blood flow, limiting the duration of time to deliver agent. Another promising strategy is to use intravascular ultrasonic imaging to guide the initial revascularization (e.g. balloon angioplasty, atherectomy, etc . . . ).

Presently the use of multiple modalities to treat a single lesion requires different catheters. In clinical practice, this means that one catheter must be removed while maintaining guide wire position after which the second catheter is tracked over the guide wire to the site of interest. The maneuver, commonly referred to as an "exchange" adds time to the procedure, increases blood loss and jeopardizes maintenance of the guide wire position.

For these reasons, it would be desirable to provide improved methods and devices for performing multiple, sequential intraluminal diagnostic and/or interventional procedures. It would be particularly desirable if such methods and devices permitted the introduction of a single catheter system employing discrete catheter components, each of which would have at least one diagnostic or interventional capability, in such a way that the components can be interchanged within the system. More particularly, it would be desirable to provide catheter components or elements having one or more diagnostic and/or interventional capabilities, where the components could be utilized in conjunction with conventional interventional and imaging catheters. Even more particularly, it would be desirable if such catheter components could provide for imaging, drug delivery, blood flow perfusion, pretreatment (e.g., slitting) of arterial plaque, and the like. All such catheters, catheter systems, and methods, should provide for rapid redeployment of each of the individual diagnostic, imaging, and interventional capabilities so that the proper treatment, diagnosis, or imaging can be performed at any point during a procedure without unnecessary delay.

2. Description of the Background Art

U.S. Pat. No. 4,976,689, describes an exchange catheter which is carried on a balloon catheter and which may include perfusion ports for maintaining blood flow through stenosed regions of the blood vessel. Other catheter perfusion systems are described in U.S. Pat. Nos. 4,661,094; 4,790,315; 5,009,636; 5,087,247; 5,163,921; and 5,180,364. U.S. Pat. Nos. 5,219,335 and 5,203,338 describe vascular catheters having reduced diameter distal ends. The '335 patents shows a dilatation balloon formed on the distal end. Catheters combining ultrasonic imaging and balloon dilatation are described in U.S. Pat. Nos. 4,841,977; 4,917,097; and 5,117,831. A catheter combining laser ablation and ultrasonic imaging is described in U.S. Pat. No. 4,576,177. A variety of intraluminal ultrasound devices is described in Bom et al. (1989) *Int. J. Cardiac Imaging* 4:79–88. Phased-array ultrasound imaging catheters are commercially available from EndoSonics, Pleasanton, Calif., as described in a brochure entitled The Cathscanner® Intracoronary Imaging System. Balloon-tipped catheters appropriate for angioplasty treatment procedures are described in, for example, U.S. Pat. No. 5,041,089, U.S. Pat. No. 4,323,071, U.S. Pat. No. 4,292,974, U.S. Pat. No. 4,762,129, and U.S. Pat. No. 4,775,371. A catheter for locally applying medication to the wall of a blood vessel or other lumen is described in U.S. Pat. No. 5,087,247, the catheter having a balloon near its distal end which is expanded with a medication, which then flows through minute holes in the balloon surface at a low flow rate. U.S. Pat. No. 4,994,033 describes an intravascular drug delivery catheter having a pair of expansion members concentrically arranged near its distal end wherein an agent is delivered to the outer expansion member, after which the inner expansion member is expanded, thereby expanding the outer member against the vessel wall and forcing the agent through minute holes in the outer member to bathe the vessel wall. U.S. Pat. No. 5,021,044 describes an intravascular drug delivery catheter having a plurality of holes on the outer surface of the catheter body through which an agent may be delivered to a site within a vessel. U.S. Pat. No. 5,112,305 describes a catheter for delivery of therapeutic agents to an interior wall of a vessel, the catheter having a balloon near its distal end with tubular extensions capable of projecting from its outer surface. An agent is delivered to the balloon which both expands the balloon and flows through the tubular extensions into the vessel wall. Other drug delivery devices are described in U.S. Pat. No. 4,693,243, U.S. Pat. No. 4,406,656, U.S. Pat. No. 5,015,232, and U.S. Pat. No. 4,850,969. An inflatable percutaneous oxygenator having a network of gas permeable fibers for oxygenating blood is described in U.S. Pat. Nos. 5,219,326. U.S. Pat. No. 4,766,337, describes a radially expandable vascular stent. U.S. Pat. No. 5,092,877, describes a self-expanding vascular stent which is carried in a sheath over an angioplasty balloon catheter.

SUMMARY OF THE INVENTION

According to the present invention, methods and apparatus are provided for sequentially performing multiple intraluminal procedures. The methods comprise introducing a sleeve catheter slidably received over a base catheter, where the base catheter includes a first interactive device which is positioned at a target location within a body lumen to perform a first procedure. The sleeve catheter is axially translated relative to the base catheter to position a second interactive device disposed on the sleeve catheter at the target location to perform a second procedure. The first and second procedures can be performed in any order (i.e. the second procedure could be performed prior to performing the first procedure) and as many times as required to complete a particular treatment, diagnosis, and/or imaging procedure.

The interactive devices can be selected from a wide variety of known interventional, therapeutic diagnostic, and imaging components and systems. For the preferred cardiovascular procedures of the present invention, the first interactive device will usually be an interventional device, such as an angioplasty balloon, an atherectomy device, a laser ablation device, or the like. The second interactive device will usually be drug delivery components, imaging systems, stent placement systems, plaque pre-slitting devices, and the like. In all cases, it will be desirable to provide perfusion ports on the sleeve catheter where the ports are spaced proximally from the distal end of the catheter by a distance sufficient to provide blood perfusion flow (i.e. blood flow through the sleeve and past an obstruction) when the sleeve catheter is in place at a desired treatment site. In that way, the sleeve can be used to provide blood perfusion in the case of abrupt reclosure and/or during prolonged interventional diagnostic, therapeutic or other procedures.

Preferred methods according to the present invention thus comprise the delivery of a therapeutic agent to a vascular treatment site in combination with an interventional procedure, such as balloon angioplasty or atherectomy. A base interventional catheter will be introduced to the target location within the patient's vascular system while the sleeve catheter is carried "piggyback" thereon. Usually, the base catheter will be used to perform the interventional procedure first, and the sleeve catheter having drug delivery capability will then be advanced over the base catheter to position the drug delivery means within the treatment site. Optionally, in the case of balloon angioplasty, the balloon catheter can be used to radially expand the sleeve so that the drug delivery means directly contacts the blood vessel wall to enhance delivery efficiency.

A preferred vascular imaging method according to the present invention comprises introducing a catheter sleeve having imaging capability while placed over an interventional base catheter, such as an angioplasty or atherectomy catheter. Usually, the imaging sleeve will be advanced to the treatment site over the interventional catheter in order to perform imaging and diagnosis of the stenotic region prior to interventional treatment. The imaging sleeve catheter will then be proximally retracted by a distance sufficient to expose the interventional component of the interventional catheter. The desired interventional procedure can then be performed, with subsequent imaging and interventional treatment steps performed as necessary.

A third preferred procedure according to the present invention combines a primary interventional or diagnostic procedure with stent or graft placement. The first interactive device can be any interventional element, imaging component, or combination thereof, usually being an angioplasty balloon. A radially expandable stent or vascular graft is carried on the sleeve catheter, typically being disposed over a radially expandable distal end thereof. After performing a conventional dilatation procedure with the angioplasty catheter, the sleeve catheter can be advanced to position the stent or graft over the angioplasty balloon within the treatment site. The balloon may then be inflated to expand and implant the stent or graft within the treatment site without the need to perform a catheter exchange.

A fourth preferred procedure according to the present invention combines a primary interventional or diagnostic procedure, preferably balloon angioplasty, with pretreatment of the arterial plaque, usually axial scoring or slitting of the plaque to enhance subsequent balloon dilation. A plurality of blades or other cutting elements is carried on the sleeve catheter, typically being fixed blades protected by retractable shields. Prior to performing balloon angioplasty, the blades on the sleeve are advanced to within the plaque and exposed or otherwise actuated to score or cut the plaque along a plurality of lines usually axially oriented, but they could be helical or any other orientation. Such scores or cuts will weaken the plaque and facilitate radial expansion and yielding of the artery during subsequent balloon dilation.

Cardiovascular treatment systems according to the present invention will comprise a sleeve catheter in combination with a base intravascular catheter, where the base intravascular catheter can be any conventional interventional or diagnostic imaging catheter. The sleeve catheter comprises a tubular body having a proximal end, a distal end, and an axial lumen therethrough which slidably receives the intravascular catheter. The sleeve catheter further includes an interactive element near its distal end, usually being an imaging system, such as a phased-array of ultrasonic transducers, a drug delivery system, such as a plurality of drug infusion tubes, a stent/graft placement system, such as a radially expandable segment on the sleeve which permits expansion and anchoring of a stent or graft by internal expansion of a balloon, or a plaque pre-slitting device. The sleeve catheter will be sized so that it fits closely over the base intravascular catheter, usually having an axial lumen with a diameter which is from 110% to 150% of the outer diameter of the intravascular catheter. Usually, the sleeve catheter will have blood perfusion ports disposed proximally of the distal end by a distance sufficient to provide blood perfusion flow when the sleeve catheter is in a stenotic or other occluded region, typically being at least 2 cm from the distal end. Optionally, in the case of drug delivery systems, stent/graft placement systems, and plaque pre-slitting devices, a portion of the sleeve in the distal region may be radially expandable to permit expansion using a balloon catheter. Such expansion during drug delivery promotes contact and enhances the efficiency of delivery into the blood vessel wall. Such expansion during stent/graft placement can act to anchor and expand the stent/graft at a target location in the vascular system. Such expansion during plaque pretreatment allows cutting blades to be contacted against the plaque to impart axial scoring or slitting.

A further understanding of the nature and advantages of the invention will become apparent by reference to the remaining portions of the specification and drawings.

BRIEF DESCRIPTION OF THE DRAWINGS

FIGS. 3A–3C illustrate the distal end of a sleeve catheter similar to that illustrated in FIG. 1, further including a vascular stent carried over its distal end.

FIGS. 6A and 6B are side elevational views of a distal portion of the catheter of FIG. 5 in undeployed and deployed configurations, respectively.

FIG. 8F is a top elevational view of a further embodiment of the stiffening element in the catheter of FIG. 5.

FIG. 9 is a side cross-section of a further embodiment of the infusion array of the catheter of FIG. 5 wherein the delivery conduits are secured to the periphery of an elastomeric sleeve.

FIG. 10A is a transverse cross-section of the infusion array of FIG. 9.

FIG. 10B is a transverse cross-section through the infusion array wherein the elastomeric sleeve is disposed external to the delivery conduits.

FIG. 12 is a side cross-section of the manifold assembly at the proximal end of the catheter of FIG. 5.

FIGS. 14A–14C are side cross-sectional views of a distal portion of the infusion catheter of FIG. 5 illustrating the radiopaque markers on the stiffening elements.

DETAILED DESCRIPTION OF SPECIFIC EMBODIMENTS

Figure 1:
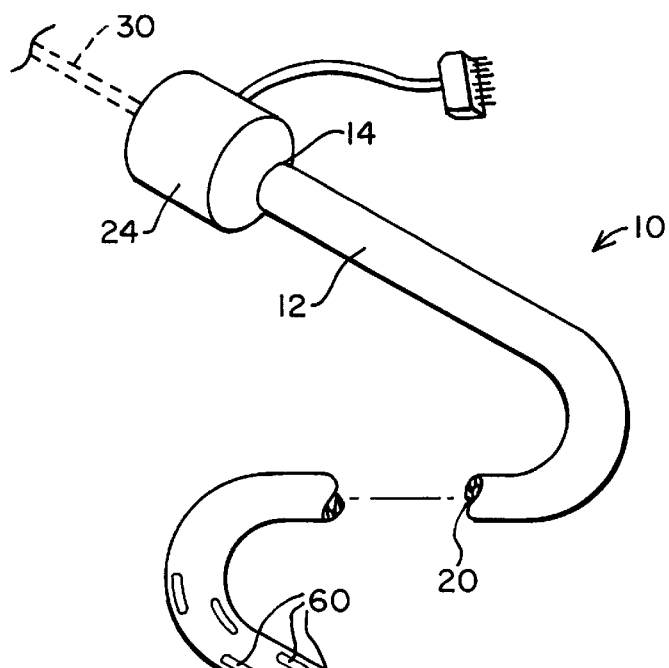
FIG. 1 is a perspective view of a sleeve catheter constructed in accordance with the principles of the present invention and including a phased-array of ultrasonic imaging transducers at its distal end.

The present invention provides methods and devices for performing multiple, sequential intraluminal procedures on a patient as part of therapeutic or diagnostic treatment. By "intraluminal," it is meant that the procedures occur at a target location within a body lumen, usually being within the patient vasculature, more usually being within the arterial system, including the coronary arteries, the peripheral arteries, and the cerebral arteries. The methods and devices of the present invention, however, are not limited to use in the vascular system, and may also be advantageously employed in other body structures, including the prostate via the prostatic urethra, (e.g. to treat benign prostatic hypertrophy, prostatitis, and adenocarcinoma), the fallopian tubes via its lumen (to treat strictures), brain parenchyma (to treat Parkinson's disease), and the like.

The "target location" within the body lumen will usually be diseased or be suspected of being diseased. In the case of vascular treatment, the target locations will usually be stenotic regions where blood flow is restricted as a result of atheroma deposits or plaque. Diseased sites within other body lumens are well-known and described in the medical literature.

By "multiple" procedures, it is meant that at least two interventional and/or diagnostic, procedures will be performed as part of a single treatment regimen. Interventional procedures may also be referred to as therapeutic and include revascularization techniques, such as balloon angioplasty, laser angioplasty, ultrasonic angioplasty, atherectomy, and the like; drug delivery techniques; stent placement techniques; axial scoring or slitting of plaque prior to dilatation by balloon angioplasty; and the like. Diagnostic procedures include imaging particularly ultrasonic imaging but also including angioscopy, contrast delivery, and the like. By "sequential," it is meant that one procedure will be performed followed by performing another without having to exchange catheters over a guidewire, usually in any order, with or without repetitions. In the preferred case of intravascular treatment, at least one of the procedures will usually be interventional, more usually being balloon, laser or ultrasonic angioplasty, or atherectomy, while the other procedure may be interventional or diagnostic usually being drug delivery, imaging, stent placement or pre-slitting of the plaque prior to angioplasty.

The methods of the present invention will utilize both a base catheter and a sleeve catheter which is slidably received over the base catheter. Each of the base and sleeve catheters will include an interactive device at or near its distal end, and the catheters will usually be introduced together with the sleeve catheter being disposed over the base catheter. Once the distal ends of the catheters reach a location near the treatment site, the catheters may be axially translated relative to each other in order to sequentially or simultaneously position each interactive device at the treatment site. Conveniently, the base catheter can be a conventional interventional or diagnostic catheter usually being an interventional catheter more usually being an angioplasty catheter or an atherectomy catheter.

The sleeve catheter is sized to be received over the base catheter and provided with an interactive capability selected to complement or enhance the interventional capability of the base catheter. For example, it will frequently be advantageous to provide an imaging sleeve catheter with either an angioplasty or atherectomy base catheter, where the imaging capability can help assess the stenotic region prior to treatment in order to provide more effective treatment. Drug delivery sleeve catheters are particularly useful to treat a target location after an angioplasty procedure in order to inhibit abrupt closure and restenosis. Radially expandable sleeve catheters permit carrying and subsequent placement of stents and grafts in combination with balloon angioplasty catheters. Alternatively, radially expandable sleeve catheters may carry cutting blades or other elements which may be deployed to score arterial plaque prior to balloon angioplasty.

The lumen of the sleeve catheter which receives the base catheter need not extend the entire length of the base catheter. Instead, a proximal portion of the sleeve catheter can consist essentially of a small diameter rod or tube, with an outside diameter typically in the range from 0.3 mm to 0.8 mm, which has sufficient flexibility to be introduced through the relatively non-tortuous regions of the vasculature but which has sufficient column strength to allow axial translation of the distal end of the sleeve. For example, stainless steel hypotube can be used, where the lumen of the hypotube provides for electrical conductor access in the case of an ultrasonic imaging device. The remaining description will be directed at embodiments where the sleeve body extends the entire length of the associated base catheter. It will be appreciated, however, that in at least some cases, a rod or narrow diameter tube can be substituted for the larger diameter tube body.

The design and construction of particular interactive devices is well-known and amply described in the patent and medical literature. For example, angioplasty devices and angioplasty catheters which may be used in the present invention are described in U.S. Pat. Nos. 5,041,089; 4,762,129; 4,775,371; 4,323,071, and 4,292,974, the full disclosures of which are incorporated herein by reference. Suitable atherectomy devices and catheters are described in U.S. Pat. Nos. 4,979,951; 5,071,425; Re. 33,569; 4,781,186; 4,926,858; 5,047,040; 5,181,920; 5,084,010; 5,226,909; 5,092,873; 5,222,966; 5,242,460; and 5,250,059, the full disclosures of which are incorporated herein by reference. Interventional laser angioplasty systems are commercially available from suppliers such as Trimedyne, Inc., Tustin, Calif., under the tradenames Optilase, Cardiolase™ and Laserprobe™. Interventional cardiovascular ultrasound systems for the destruction of plaque are described in U.S. Pat. Nos. 3,565,062 and 4,692,139, and WO93/21835, the full disclosures of which are incorporated herein by reference, and Siegel et al. (1990) J. Am. Col. Cardiol. 15:345–351. Imaging devices suitable for use as the interactive device of the present invention will usually be ultrasonic, phased-array devices, such as described in U.S. Pat. Nos. 4,841,977 and 4,917,097, the full disclosures of which are incorporated herein by reference. Intravascular stents and stent delivery catheters are described in U.S. Pat. Nos. 4,776,337 and 5,092,877, the full disclosures of which are incorporated herein by reference.

Referring now to FIG. 1, the sleeve catheter 10 comprises a tubular body 12 having a proximal end 14 and a distal end 16. Sleeve catheter 10 includes an axial lumen 20 which extends from a distal port 22 to a proximal housing 24. The axial lumen 20 will be sized to receive a base catheter, such as angioplasty catheter 30 shown in broken line. The axial lumen 20 will typically be sized slightly larger than the outside diameter of the associated base catheter, typically having an inner diameter which is from 110% to 150% of the outer diameter of the base catheter, preferably being from 110% to 120% of the diameter of the base catheter. Thus, the lumen 20 will typically be sized from about 1.3 mm to 2.0 mm, more usually from 1.3 mm to 1.7 mm. The catheter body 12 will have a length depending on its desired use. Typically, the length will be from about 40 cm to 150 cm, usually being between about 40 cm and 120 cm for peripheral catheters and being between about 110 cm and 150 cm for coronary sleeve catheters. The outer diameter of the catheter body will usually be between about 1.4 mm and 2.3 mm, more usually being between about 1.6 mm and 2.0 mm.

The catheter body may be composed of a wide variety of biologically compatible materials, typically being made from natural or synthetic polymers, such as silicone rubber polyethylene, polyvinylchloride, polyurethanes, polyesters, polytetrafluorethylene's (PTFE's), nylon, and the like. Optionally, the catheter sleeve body may be formed as a composite having one or more reinforcement layers incorporated within the polymeric body in order to enhance its strength, flexibility, and toughness. Additionally, the catheter sleeve may include an inner liner made from a lubricous material such as a fluoropolymer, e.g. PTFE, FEP, or PFA, to enhance its ability to slide over the base catheter. Additionally, the composition of the catheter body 12 may vary along its length, with discrete portions of its length being composed from different materials and/or composites. Typically, the catheter body will be formed using extrusion techniques which are well described in the patent and medical literature.

An exemplary catheter 10 (FIG. 1) includes an imaging array 32 formed over a portion of the outer surface of the body near its distal end. The imaging array comprises a plurality of circumferentially spaced-apart elongate ultrasonic transducers, which are conveniently formed by depositing a polymeric or other transducer material onto the outer surface of the catheter body. The resulting ultrasonic transducers should be capable of operating at a frequency in the range from about 5 to 50 MHz, with suitable piezoelectric materials including polyvinylidene difluouride (PVDF) and vinylidene fluoride-trifluoroethylene copolymers. Suitable inorganic transducer materials include barium titanate and cinnabar. Particular designs and methods for incorporating phased-array ultrasonic transducer devices into the sleeve catheter 10 are well described in the patent and scientific literature, including the U.S. patents which have been incorporated by reference hereinabove.

Figure 2:
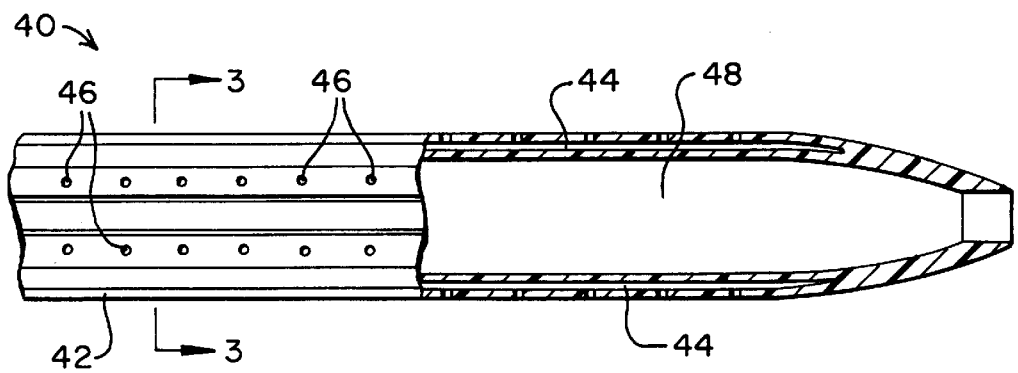
FIG. 2 is the distal end of a sleeve catheter similar to that illustrated in FIG. 1, further including a plurality of drug infusion lumens are provided at its distal end.

A sleeve catheter 40 intended for intravascular drug delivery is illustrated in FIGS. 2 and 2A. The catheter 40 includes a catheter body 42 having the general dimensions and being fabricated by the methods described above. The catheter body 42 further includes a plurality of infusion lumens 44 formed axially along its length. The infusion lumens communicate with a plurality of drug-infusion ports 46 disposed near the distal end of the catheter 40. The catheter 40 includes axial lumen 48, which may receive a balloon angioplasty or other interventional catheter, generally as described above.

Figure 3:
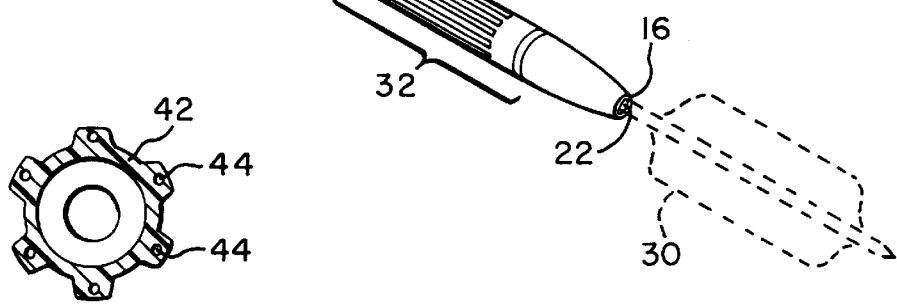
FIG. 3 is a cross-sectional view of the catheter of FIG. 2, taken along line 3—3.

A sleeve catheter 300 for intravascular stent or graft placement is illustrated in FIGS. 3A–3C. The sleeve catheter 300 comprises a tubular body 302 having a radially expandable region 304 near its distal end 306. The radially expandable region 304 may be composed of an elastomeric material and/or have a plurality of axial slits 308 which facilitate expansion by internal inflation of an angioplasty balloon. Optionally, the sleeve catheter 300 includes perfusion ports 301, as described previously.

An expandable stent 310 is disposed over the radially expandable region 304. The stent structure is illustrated as multiple, counter-wound helices, where the helices ar non-elastically deformable so that they may be expanded from a reduced diameter configuration, as illustrated in FIG. 3A to an enlarged diameter configuration as illustrated in FIG. 3C. Other stent structures, such as thin-walled tubes which have been etched or cut along a plurality of axial and/or circumferential lines to permit radial expansion (see U.S. Pat. Nos. 4,776,337 and 5,236,447, the full disclosures of which are incorporated herein by reference), will also be useful with the present invention, as will be vascular graft structures which are employed in treating aortic and other aneurysms.

The stent placement sleeve catheter 300 will usually be introduced together with an angioplasty balloon catheter 320 over a guidewire GW in a conventional manner. The sleeve catheter 300 may be introduced simultaneously with the angioplasty catheter 320 or may be introduced subsequent to the initial introduction of the angioplasty catheter. Usually, balloon 322 will be expanded to treat a target region in blood vessel BV while the sleeve catheter 300 remains just proximal to the balloon, as illustrated in FIG. 3A (with the expanded balloon shown in broken line). After treatment, the balloon 322 will be deflated and the sleeve catheter 300 will be advanced over the angioplasty catheter 320 so that the expandable region 304 lies over deflated balloon 322, as illustrated in FIG. 3B. Alternatively, after deflation, the balloon 322 on angioplasty catheter 320 may be retracted to lie within the radially expandable region 304 of sleeve catheter 300, typically by aligning radiopaque markers (not shown) on both the angioplasty catheter 320 and the sleeve catheter 300. The angioplasty catheter 320 and sleeve catheter 300 may then be advanced simultaneously until the expandable region 304 carrying stent 310 lies within the target region which has just been treated. In either case, the balloon 322 is then expanded, causing expansion of the region 304 and the stent 310, as illustrated in FIG. 3C. The balloon 322 may then be deflated leaving the expanded stent anchored in place at the treatment site.

Figure 4A:
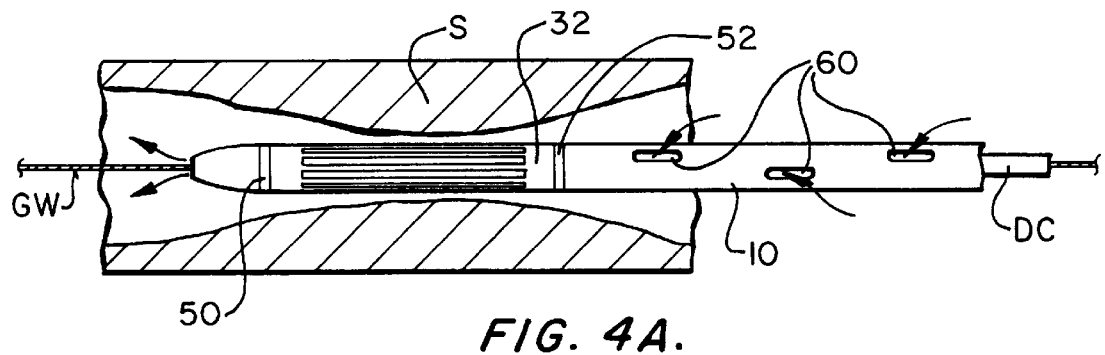
FIGS. 4A–4D are side views illustrating the sleeve of FIG. 1 being used in combination with a balloon angioplasty catheter for the imaging and dilatation of a region of stenosis in a blood vessel.

Referring now to FIGS. 4A–4D, use of the imaging sleeve catheter 10 in performing vascular imaging in combination with a balloon angioplasty procedure will be described. The imaging sleeve 10 is introduced into a region of stenosis S while disposed over a conventional dilatation catheter DC. The combination of the imaging sleeve 10 and the dilatation catheter DC is introduced over a conventional guidewire GW until the imaging device 32 is located within the region of stenosis S. Conveniently, radiopaque markers 50 and 52 may be provided in order to facilitate positioning and locating the imaging portion of the sleeve under fluoroscopic viewing. The initial position of the imaging sleeve 10 used for imaging the region of stenosis S is illustrated in FIG. 4A.

Figure 4B:
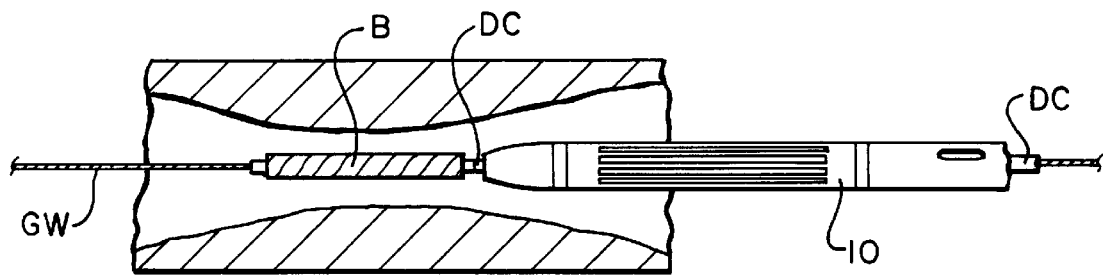

After imaging, the imaging sleeve 10 is withdrawn over the dilation catheter DC by a distance sufficient to expose dilation balloon B, as illustrated in FIG. 4B. After exposing the dilatation balloon B, the dilatation catheter DC can be more precisely positioned (with the help of radiopaque markers) to effect dilatation in the conventional manner. It will be appreciated that the information gained from imaging will be useful in assessing the severity of the lesion and in choosing the most appropriate treatment protocol.

Figure 4C:
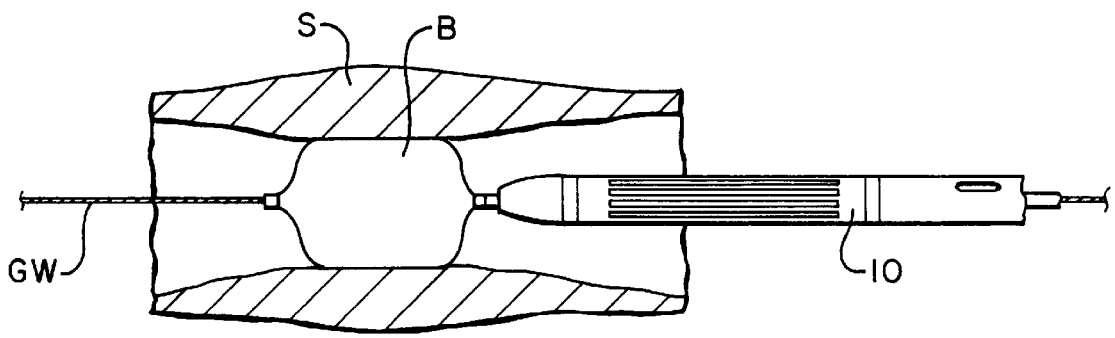
Figure 4D:
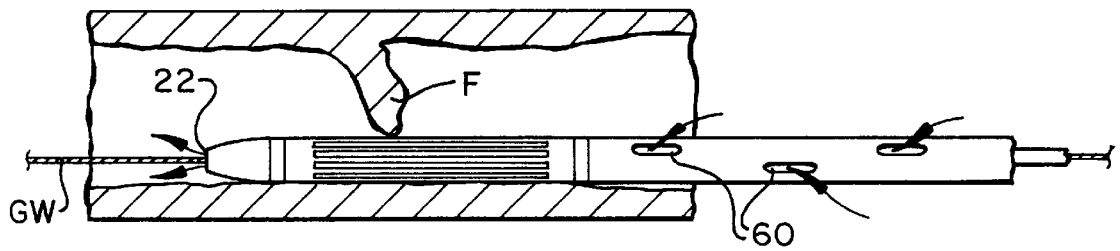

Inflation of the dilatation balloon B is illustrated in FIG. 4C. The balloon expands radially outward to distend the blood vessel at the treatment site to restore blood flow in a conventional manner. After treating the region of stenosis S using the dilatation catheter DC, the imaging sleeve 10 remains available for reimaging the treated region by simply passing the sleeve distally over the deflated balloon B of the dilatation catheter DC until it is properly positioned for imaging. The imaging sleeve 10 is also available for providing perfusion blood flow in the case of abrupt vessel closure, as illustrated in FIG. 4D. Balloon dilatation can sometimes cause dissection in the blood vessel wall, resulting in the formation of "flaps" F of material which can potentially occlude the blood vessel lumen. In such cases, blood flow through the vessel can be abruptly stopped. Thrombus or blood clot formation at the site of the lesion can also cause abrupt blood vessel closure. In the case of coronary arteries, such cessation of blood flow can lead to a myocardial infarction and be life threatening. The imaging sleeve 10 of the present invention also permits blood flow to be reestablished, even in the case of abrupt closure, by providing perfusion ports 60 on the tubular body of the catheter proximal of the imaging region 32. The perfusion ports 60 are provided in sufficient number and along a sufficient length so that at least some of said ports will be available to permit the inflow of blood upstream of the region of stenosis and any obstructions which may occur therein. As illustrated in FIG. 4D, the blood flows into these ports and flows out of the distal port 22, providing the desired blood perfusion flow. Blood flow perfusion through the sleeve catheter can be enhanced by partially withdrawing the angioplasty catheter to open the internal lumen between the ports 60 and the open distal port 22.

In a further embodiment, illustrated in FIGS. 5-14, an agent infusion catheter 200 is configured to slidably receive a conventional dilatation catheter within an axial guide passage in the infusion catheter shaft. This allows the dilatation catheter to serve as a guide member for the infusion catheter to guide the catheter to the treatment site and permits the use of any of a variety of commercially-available dilatation catheters in conjunction with the agent infusion catheter of the invention. Dilatation catheters suitable for use with the infusion catheter illustrated in FIGS. 5–14 are described, for example, in U.S. Pat. No. 5,041,089, U.S. Pat. No. 4,323,071, U.S. Pat. No. 4,292,974, U.S. Pat. No. 4,762,129 and U.S. Pat. No. 4,775,371, the complete disclosures of which are incorporated herein by reference. Such dilatation catheters are commercially available from, for example, Advanced Cardiovascular Systems, Inc., Temecula, Calif.

Figure 5:
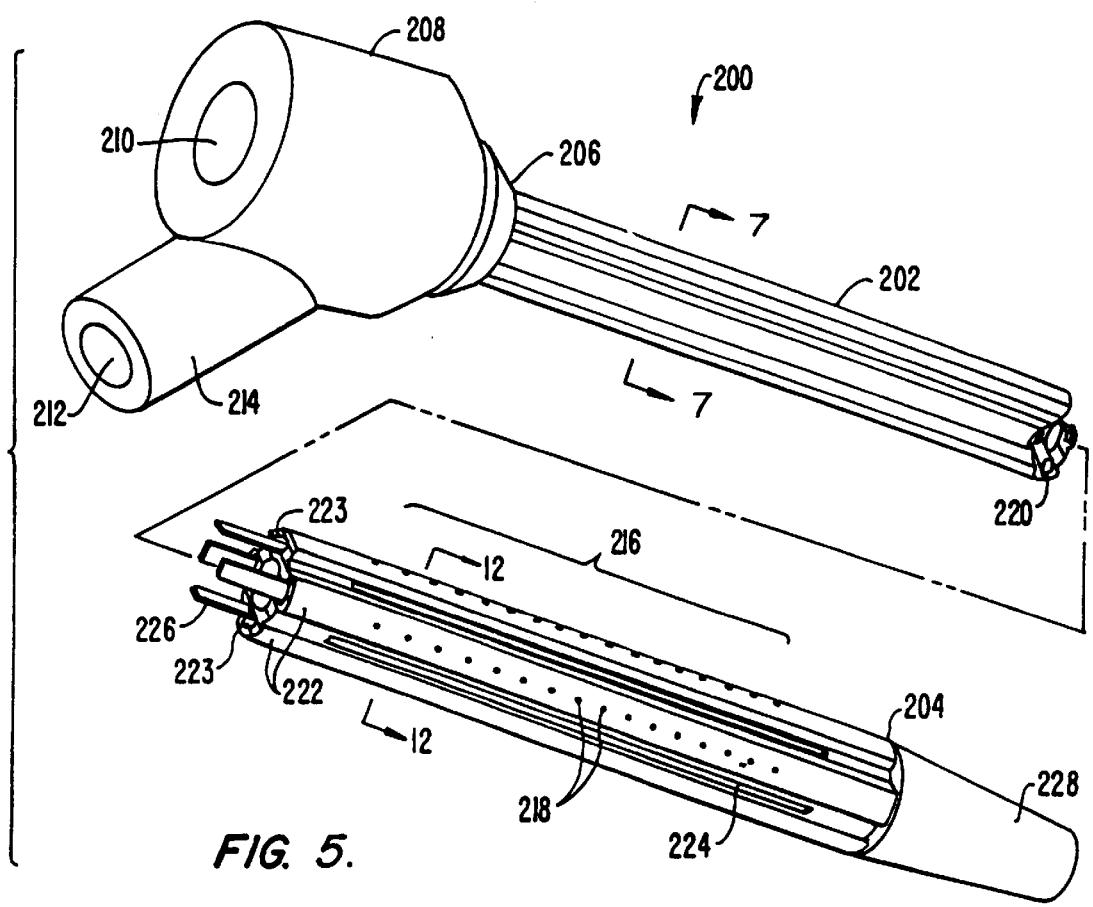
FIG. 5 is a perspective view of a further embodiment of an agent delivery catheter constructed in accordance with the principles of the invention.

Referring to FIG. 5, in a preferred embodiment, agent infusion catheter 200 includes an elongate flexible shaft 202 having a distal end 204 and a proximal end 206. A manifold assembly 208 is fixed to the proximal end of the shaft and includes dilatation catheter port 210 on its proximal end and an agent introduction port 212 in a fitting 214 provided with a Luer lock (not shown), secured to the assembly. At the distal end of the shaft 202 is an infusion array 216 having a plurality of orifices 218 along lateral surfaces of the shaft. Shaft 202 comprises a plurality of axially disposed agent delivery passages 220 extending from the proximal end which are connected to a corresponding number of agent delivery conduits 222 at the distal end. Orifices 218 are in communication with interior axial lumens 233 in delivery conduits 222. An axial cut or slot 224 is formed in shaft 202 between each of delivery conduits 222 such that the delivery conduits are separated from one another by the slots. A stiffening element 226 is disposed in at least a single delivery conduit 222, as described more fully below. A conically tapered distal tip 228 is fixed to the distal end 204 of the shaft.

In a preferred embodiment, shaft 202 will be constructed of materials and will have dimensions selected as appropriate for insertion of the shaft transluminally inside a guiding catheter (not shown), in a blood vessel. In an exemplary embodiment, shaft 202 will have a length in the range of 110 to 150 cm, and an outer diameter of 1.1 mm–2.3 mm (0.04 to 0.09 inches). Infusion array 216 will be approximately 10 to 60 mm in length. Catheter shaft 202 may be any of a variety of biocompatible, flexible materials including, for example, polyester, polyethylene or polyamide. Preferably, as described above, catheter shaft 202 (including delivery passages 220) and delivery conduits 222 will comprise a single, monolithic extrusion from proximal end 206 to distal end 204.

As shown in FIG. 6A, in an undeployed configuration, infusion array 216 is aligned with and has an outer diameter generally equal to that of the proximal portion of shaft 202. As shown in FIG. 6B, a dilatation catheter 230 may be positioned through an axial guide passage of shaft 202 (described below) such that a balloon or other expansion member 232 at the distal end of the dilatation catheter is within infusion array 216 adjacent delivery conduits 222. By expanding balloon 232, infusion array 216 is deployed radially outward to bring orifices 218 adjacent to a treatment site on a vessel wall.

Figure 7:
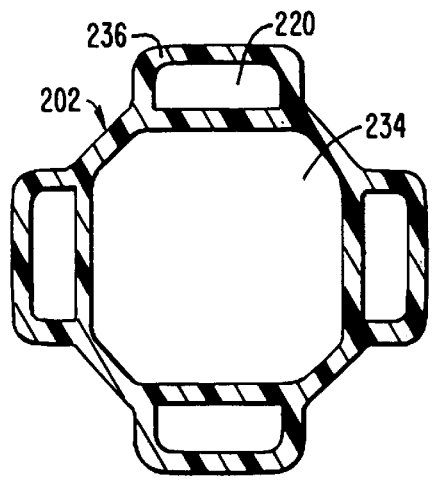
FIG. 7 is a transverse cross-section through line 7—7 in a proximal portion of the shaft of the catheter of FIG. 5.

FIG. 7 illustrates a transverse cross-section through a proximal portion of shaft 202. A guide passage 234 extends longitudinally through the catheter shaft for slidably receiving a dilatation catheter. Guide passage 234 may be coated with a lubricous material such as a hydrogel or fluorocarbon polymer, for example, fluorinated ethylene-propylene or polytetrafluoroethylene, available commercially under the trademark Teflone from DuPont. Such a coating facilitates longitudinal positioning and alignment of a dilatation catheter in guide passage 234 when catheter 200 is disposed in a tortuous configuration in a vessel. Guide passage 234 will have a diameter of 0.7–2.0 mm (0.03–0.08 inches), preferably 1.2–1.8 mm (0.05–0.07 inches), suitable for receiving most commercially-available dilatation catheters in current use.

Delivery passages 220 run parallel to guide passage 234. In an exemplary embodiment, delivery passages 220 are disposed in longitudinal ribs 236 which protrude radially outward from shaft 202. Delivery passages 220 will have an interior height (or diameter, if round) in the range of 0.01 mm to 0.7 mm (0.005–0.03 inches).

Figure 8A:
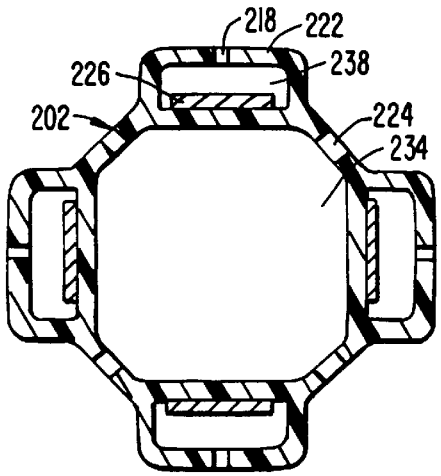
FIGS. 8A–8E are transverse cross-sections through line 8—8 at the distal end of the shaft in the catheter of FIG. 5 illustrating various embodiments of the stiffening elements in the infusion array.

FIGS. 8A–8E illustrate transverse cross-sections of the distal portion of shaft 202 through infusion array 216 in various embodiments. In the embodiment of FIG. 8A, delivery conduits 222 are separated from each other by slots 224 so as to permit lateral expansion for deployment of the delivery conduits. Delivery conduits 222 have an axial lumen 238 which is in communication with delivery passages 220 in the catheter shaft. Delivery conduits 222 surround guide passage 234. Stiffening elements 226 are disposed within axial lumen 238 and occupy only a portion thereof to permit flow of agent through the lumen. In the embodiment of FIG. 8A, stiffener elements 226 comprise ribbon or bar-shaped rods of generally rectangular cross-section. The rods may be unrestrained in the axial lumens of the delivery conduits, secured at their distal end to the distal tip as described below, or co-extruded in the walls of the delivery conduits, also described below. Stiffener elements 226 may be any of a variety of materials such as stainless steel, tantalum, nickel-titanium, or tungsten and having a geometrical configuration leading to greater axial rigidity but being laterally more flexible and resilient. The stiffening elements may extend from distal end 204 to proximal end 206 of shaft 202 through the delivery passages, or may have a shorter length, e.g. 30–70 mm, so as to extend from a point near distal end 204 to a point just proximal to infusion array 216.

Stiffener elements 226 serve several functions. First, the stiffener elements help to maintain the patency of axial lumens 238 in the delivery conduits. Second, stiffener elements 226 provide stiffness and resilience to delivery conduits 222 such that, following expansion of the delivery conduits, they will recoil back to the undeployed configuration. Third, stiffener elements 226 serve to maintain the relative alignment between the delivery conduits during longitudinal positioning and later expansion, so that the delivery conduits remain approximately equally separated from each other when deployed, facilitating uniform treatment of an area of the vessel wall. Furthermore, a stiffener element 226 of rectangular cross-section allows controlling the relative magnitude of lateral versus radial stiffness. In the configuration shown, the bending stiffness of stiffener element 226 is substantially less in the radial direction about a first axis perpendicular to the shaft than in the lateral direction about a second axis perpendicular to the shaft and perpendicular to the first axis.

Figure 8B:
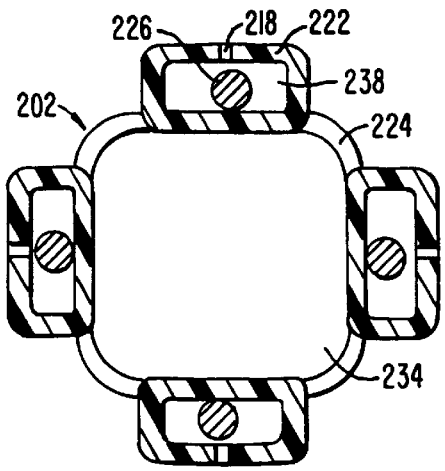

FIG. 8B illustrates a further embodiment of delivery conduits 222 and stiffening elements 226. In this embodiment, slot 224 is significantly wider than in previous embodiments, such that substantially all of the material between delivery conduits 222 is removed. Further, in this embodiment, stiffener elements 226 comprise rods having a round cross-section. With such a shape, the stiffener elements are particularly effective in maintaining the patency of axial lumen 238. Further, the stiffener elements of round cross-section will not tend to block passage of an agent through orifices 218 if the rods float to the outer surface of the axial lumen.

Figure 8C:
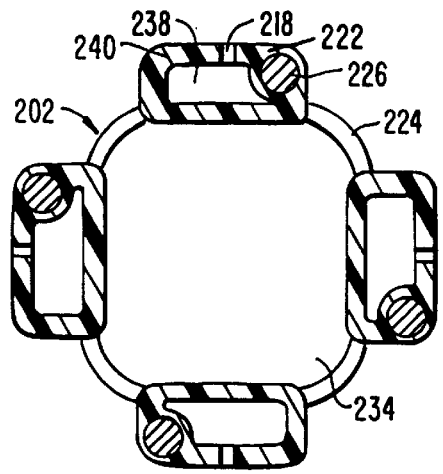

In the embodiment of FIG. 8C, stiffener elements 226 comprise rods round in cross-section embedded in the outer wall 240 of delivery conduit 222. It should be understood that stiffener elements of various cross-sectional shapes may be embedded in the wall of the delivery conduits in the manner shown in FIG. 8C.

Figure 8D:
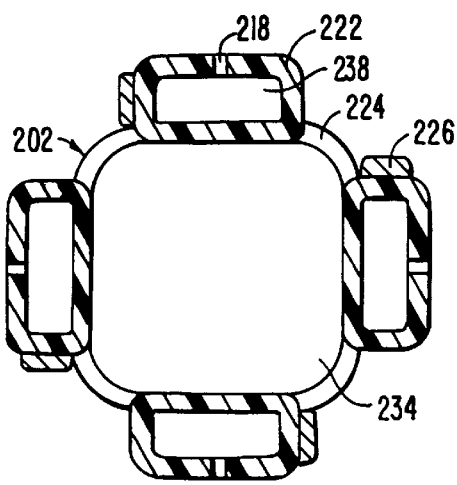

In the embodiment of FIG. 8D, stiffener elements 226 are disposed exterior to delivery conduits 222. In an exemplary embodiment, the stiffener elements are disposed along a side surface of each delivery conduit so as not to interfere with contact between the outer lateral surfaces of the delivery conduits and the wall of the vessel. Again, stiffener elements of various configurations may be used, including round, rectangular, and other cross-sectional shapes.

Figure 8E:
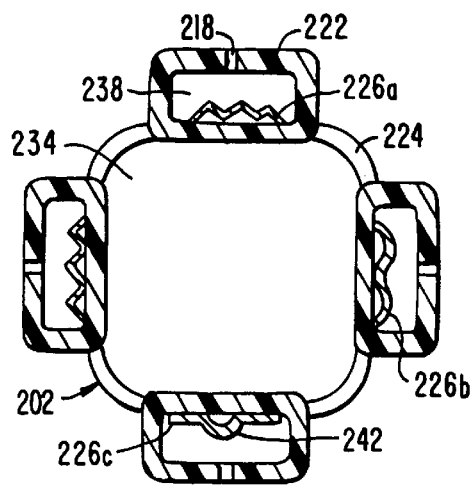

In FIG. 8E, several additional embodiments of stiffener elements 226 are illustrated. In these embodiments, the stiffener elements have a surface contour which prevents the stiffener elements from blocking flow of agent through orifices 218 should the stiffener elements float outward against the outer wall of the axial lumen. In one embodiment, stiffener element 226a has a zigzag cross-section. In a second embodiment, stiffener element 226b has a double curve or wave cross-section. In a third embodiment, stiffener element 226c has a longitudinal ridge 242. In these embodiments, a plurality of transverse slots (not shown) may be provided at various points along the length of the stiffener elements to reduce radial stiffness and enhance the free flow of agent from one side of the stiffener element to the other.

In another exemplary embodiment, illustrated in FIG. 8F, stiffener elements 226 will have a plurality of cut-outs 227 along their length, which may take the form of indentations along the longitudinal edges as shown, or, alternatively, slots or holes through a middle portion of the stiffener elements. Cut outs 227 facilitate flow of agent from one side of the stiffener elements to the other to ensure the agent is not blocked from flowing through orifices 218.

In a further embodiment of infusion array 216, illustrated in FIGS. 9 and 14A, an elastomeric sleeve 248 is mounted in guide passage 234, with delivery conduits 222 disposed about the periphery of the elastomeric sleeve. Elastomeric sleeve 248 will comprise a tubular element of a flexible and resilient elastomeric polymer, such as silicon or urethane. Usually, delivery conduits 222 will be fixed to the exterior of elastomeric sleeve 248. In this way, the elastomeric sleeve serves to facilitate resilient return of the delivery conduits from the deployed to the undeployed position. In addition, the elastomeric sleeve serves to maintain alignment of the delivery conduits as they are expanded so as to maintain proper spacing between adjacent delivery conduits. While stiffener elements 226 are included in FIGS. 9 and 10, the use of elastomeric sleeve 248 may obviate the need for stiffening elements, as the sleeve may adequately maintain alignment and provide resilience.

In an alternative embodiment, illustrated in FIG. 10B, elastomeric sleeve 248 is disposed external to delivery conduits 222, with the delivery conduits secured to the interior of the sleeve. Orifices 218 extend from axial lumen 238 through delivery conduits 222 as well as through elastomeric sleeve 248. In a preferred embodiment, the elastomeric sleeve is configured so as to generally conform to the exterior contour of the delivery conduits, minimizing the profile of the distal portion of the catheter, as well as accommodating the expansion of the delivery conduits.

Figure 11A:
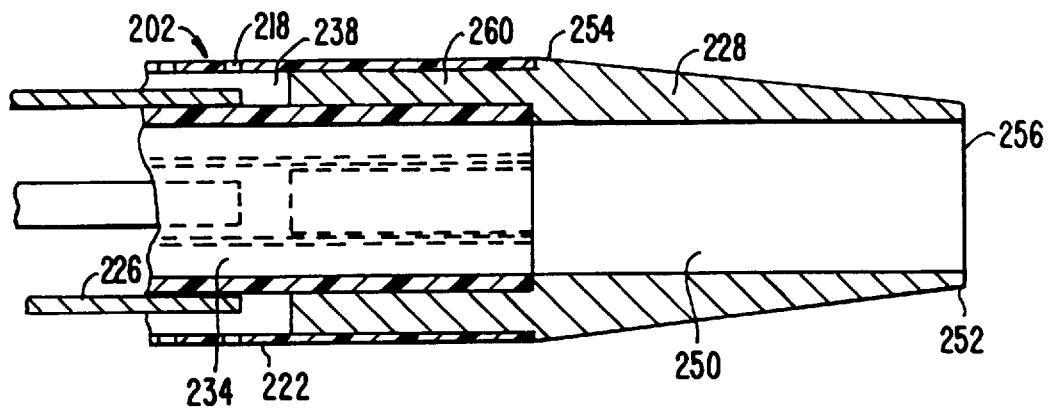
FIGS. 11A–11B are a side cross-section and a perspective view, respectively, of the distal tip of the catheter of FIG. 5.
Figure 11B:
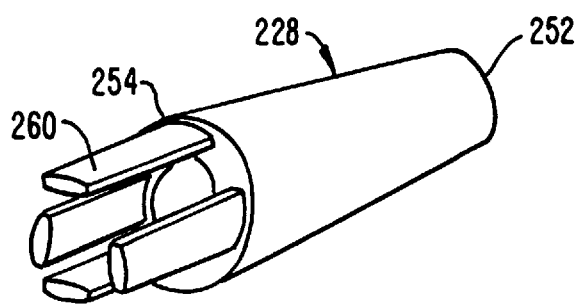
Figure 11C:
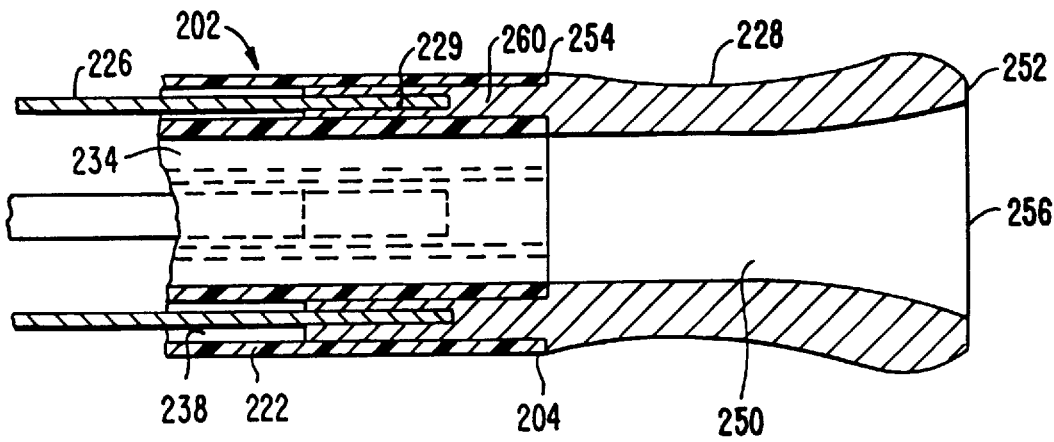
FIG. 11C is a side cross-sectional view of a further embodiment of a distal tip constructed in accordance with the principles of the invention.

Referring now to FIGS. 11A–11C, distal tip 228 will be more fully described. Distal tip 228 provides a minimally traumatic leading edge to catheter 200, as well as facilitates slidable tracking of catheter 200 over a dilatation catheter, as described more fully below. In addition, the distal tip 228 provides a seal for the distal ends of delivery conduits 222. In an exemplary embodiment, shown in FIGS. 11A–11B, distal tip 228 has an axial passage 250 aligned with guide passage 234 in shaft 202. Distal tip 228 has a conically tapered exterior to enhance navigation of the catheter through a vessel lumen. Usually, distal tip 228 will have a length of 1 to 5 mm and exterior diameter at proximal end 254 generally equal to that of the outer surface of the delivery conduits 222, with distal end 252 being approximately 30% smaller in diameter than proximal end 254. Distal tip 228 further includes a plurality of proximally-extending prongs 260, which fit within axial lumens 238 at the distal ends of delivery conduits 222. Prongs 260 thereby provide a seal for the distal end of the delivery conduits and provide the adhesion to shaft 202 required to properly retain distal tip 228 with the catheter. Prongs 260 can also be employed to retain the distal ends of stiffener elements 226 within axial lumens 238. In one embodiment, distal tip 228 may be molded urethane, formed by a process in which urethane is poured into a mold and the distal end of shaft 202 is inserted into the mold while the urethane is liquid, permitting the urethane to wick into axial lumens 238, thereby forming prongs 260.

In an alternative embodiment of the distal tip, illustrated in FIG. 11C, distal tip 228 has a trumpet shape wherein axial passage 250 tapers radially outward in the distal direction. The outer periphery of distal tip 228 may be tapered inward near the distal end 252 to facilitate navigation through a vessel lumen. The trumpet-shaped distal tip of FIG. 11C facilitates smooth retraction of the expansion member (e.g. balloon) of a dilatation catheter from a position distal to distal tip 228 to a position within guide passage 234 adjacent delivery conduits 222.

FIG. 11C further illustrates the retention of distal ends 229 of stiffener elements 226 by encapsulation in prongs 260 of the distal tip. In this embodiment, when distal tip 228 is to be formed, stiffener elements 226 are positioned in axial lumens 238 of the delivery conduits with distal ends 229 near the distal end 204 of shaft 202. Distal tip 228 is then formed as described above, by pouring a polymer such as urethane into a mold and putting the distal end of the catheter shaft in the mold while the urethane is liquid. The urethane then wicks into axial lumens 234, encapsulating the distal ends of the stiffener elements.

Referring now to FIG. 12, manifold assembly 208 will be more fully described. The manifold assembly includes a housing 262 which may be a metal or any of a variety of rigid plastics, including acrylonitrile-butadiene-styrene (ABS), Delrin®, polycarbonate and the like. Shaft 202 extends through a flexible polymeric strain relief 264 into an interior chamber 266 within housing 262. The proximal end 270 of shaft 202 is secured about a cylindrical mandrel 272 formed in housing 262. Mandrel 272 has an axial bore 274 which connects dilatation catheter port 210 to guide passage 234. In a preferred embodiment, a diaphragm 275 is mounted in a proximal portion of bore 274 near catheter port 210. Diaphragm 275 has a passage 277 which may comprise a hole or slit which elastically expands when a dilatation catheter of larger diameter is inserted through it. The diaphragm thus provides a sealed entrance for introducing a dilatation catheter into guide passage 234.

Chamber 266 is in communication with agent introduction port 212 in Luer fitting 214. The proximal end of shaft 202 will have circumferential notches 268 providing fluid communication between chamber 266 and agent delivery passages 220. Luer fitting 214 will be configured for connection to a precision agent delivery device. In this way, an agent delivered through delivery port 212 will flow into delivery passages 220 for delivery to infusion array 216.

Use of catheter 200 is illustrated in FIGS. 13A–13D. In this embodiment, utilizing the agent infusion catheter 200 described above in connection with FIGS. 5–12, a balloon dilatation catheter DC of conventional construction is transluminally positioned in a blood vessel V such that a balloon or other expansion member 280 (in an uninflated configuration) is near a treatment site S. Typically, dilatation catheter DC will be positioned over a movable flexible guide wire GW. During this step, agent infusion catheter 200 need not be, but may be, positioned slidably over dilatation catheter DC. In some embodiments, it would be desirable to position a dilatation catheter in the vessel first, do a dilatation and then remove the dilatation catheter. Subsequently, catheter 200 is introduced over the dilatation catheter and both catheters are introduced together into the vessel. In other instances, catheter 200 will be positioned over the dilatation catheter outside of the body, and both catheters will be transluminally positioned in the vessel together. The dilatation catheter may then be used to perform dilatation as described below.

Figure 13A:
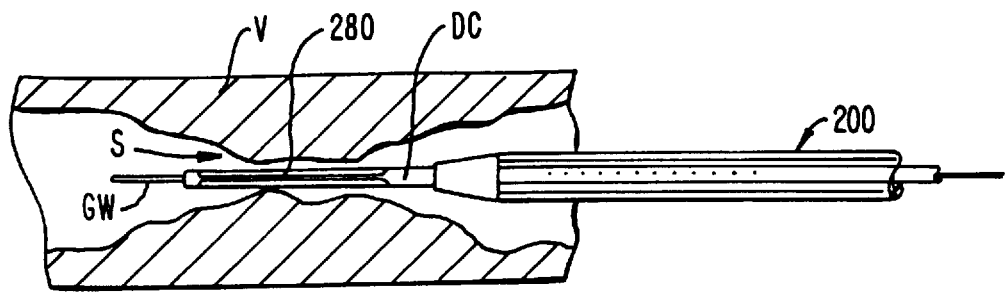
FIGS. 13A–13D are side views illustrating the catheter of FIG. 5 positioned in a body lumen according to the method of the invention.
Figure 13B:
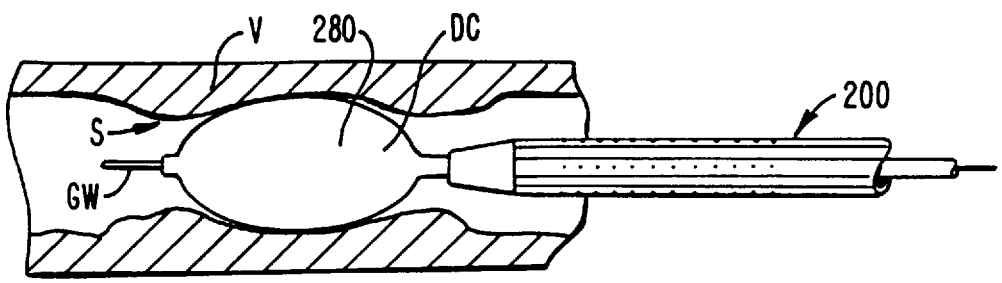

As shown in FIG. 13B, balloon dilatation catheter DC is positioned such that expansion member 280 is disposed distal to the distal end of agent infusion catheter 200. Expansion member 280 is then inflated using known techniques, dilatating vessel V at treatment site S.

Figure 13C:
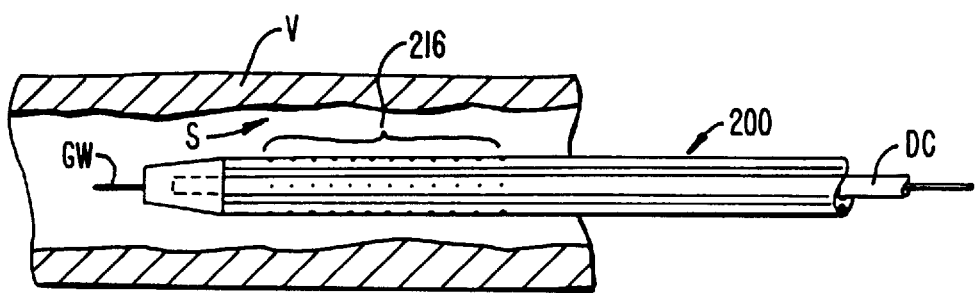
Figure 13D:
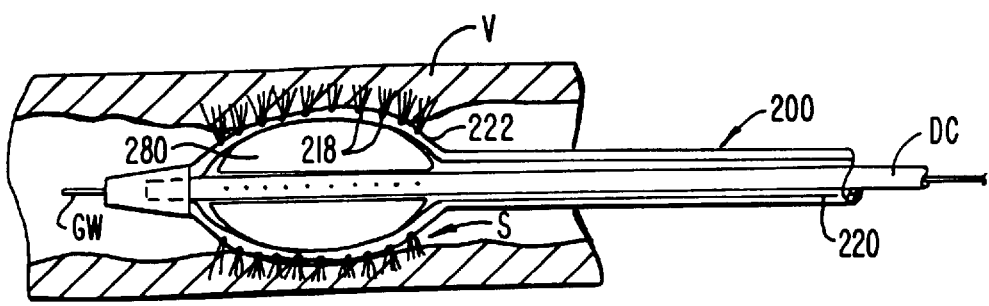

Expansion member 280 is then deflated and, as shown in FIG. 13C, dilatation catheter DC is drawn proximally relative to agent infusion catheter 200. Dilatation catheter DC is positioned such that expansion member 280 is adjacent infusion array 216 in the interior guide passage of catheter 200, described above. Agent infusion catheter 200 is then positioned within vessel V such that infusion array 216 is near treatment site S.

Expansion member 280 is then inflated so as to position delivery conduits 222 in apposition to treatment site B on the vessel wall. An agent is then delivered through delivery passages 220 in catheter 200 to delivery conduits 222. The agent is infused under pressure through the delivery conduits and through orifices 218 to penetrate the vessel wall in the region of treatment site S. When treatment is complete at the site, agent delivery is discontinued, and expansion member 280 deflated to return delivery conduits 222 to an undeployed position as in FIG. 13C. If further treatment is desired at the same or different site, dilatation catheter DC may be extended distal to infusion catheter 200 to the position shown in FIG. 13A. Dilatation and/or agent infusion may be repeated at the same or a different site.

To facilitate longitudinal positioning of infusion catheter 200 in a vessel lumen, as well as to assist proper axial alignment of the expansion member (e.g. balloon) of the dilatation catheter with infusion array 216, radiopaque markers may be provided on infusion catheter 200. In a preferred embodiment, shown in FIGS. 14A–14C, radiopaque markers 282 are disposed on one or more of stiffener elements 226. Markers 282 are formed by, for example, plating a radiopaque material such as gold or platinum onto stiffener elements 226. Dilatation catheter DC will also have a radiopaque marker 284, which is typically formed on the inner shaft 286 of catheter DC in the interior of expansion element 280. In one embodiment, shown in FIG. 14A, at least two markers 282 are disposed on stiffener elements 226 in a central portion of infusion array 216, the markers being separated a distance from one another usually about equal to or slightly greater than the length of marker 284 on dilatation catheter DC. In this way, by visualization through a radiographic imaging device, markers 282 facilitate axial alignment of expansion element 280 with infusion array 216 by aligning dilatation catheter marker 284 between markers 282 on stiffener elements 226. Markers 282 further provide visual indication of the location of infusion catheter 200 within the vessel so that infusion array 216 may be positioned adjacent to a treatment site.

Alternative embodiments of radiopaque markers 282 are illustrated in FIGS. 14B and 14C. In FIG. 18B, marker 282 is disposed on a distal portion of stiffener element 226. In this way, dilatation catheter DC and/or infusion catheter 200 are axially re-positioned relative to one another until marker 284 on the dilatation catheter is exposed on the proximal side of marker 282. In the embodiment of FIG. 14C, marker 282 is disposed on a proximal portion of stiffener element 226 whereby the catheters are axially aligned by positioning dilatation catheter marker 284 distal to marker 282 on the stiffener element.

While the above is a complete description of the preferred embodiments of the invention, various alternatives, modifications, and equivalents may be used. Therefore, the above description should not be taken as limiting the scope of the invention which is defined by the appended claims.

Although the foregoing invention has been described in some detail by way of illustration and example, for purposes of clarity of understanding, it will be obvious that certain changes and modifications may be practiced within the scope of the appended claims.

What is claimed is:

1. A method for delivering a therapeutic agent to a blood vessel in combination with another therapeutic procedure, said method comprising:

introducing a base catheter having a therapeutic device at a distal end thereof and a sleeve catheter slidably disposed thereover to a stenotic region in the blood vessel, wherein the therapeutic device is selected from the group consisting of a dilatation balloon, a cutting element, a laser, and an ultrasonic transducer, and the first procedure comprises revascularization of a stenosed region in a blood vessel;

performing a therapeutic procedure at the stenotic region with the therapeutic device while a distal end of the sleeve catheter is proximally retracted to expose said therapeutic device;

positioning the sleeve catheter over the base catheter to align an infusion matrix on the sleeve catheter for delivering the therapeutic agent at the stenotic region; and delivering therapeutic agent to said stenotic region through the infusion matrix on the sleeve catheter while said sleeve catheter remains positioned over the base catheter.

2. A method as in claim 1, wherein the base catheter comprises a balloon catheter and the therapeutic procedure comprises angioplasty.

3. A method as in claim 2, wherein the sleeve catheter is aligned with the balloon of the balloon catheter within the stenotic region, further comprising inflating the balloon to contact the infusion matrix on the sleeve against the stenotic region, and delivering the therapeutic agent while contact is maintained between the infusion matrix and the stenotic region.

4. A method as in claims 2 or 3, wherein the infusion matrix on the sleeve catheter is aligned with the balloon of the balloon catheter and the therapeutic agent is delivered after performing the angioplasty procedure.

5. A method for imaging a blood vessel during a therapeutic procedure, said method comprising:

introducing a base catheter having a therapeutic device at a distal end thereof and a sleeve catheter slidably disposed thereover to a target location in the body lumen;

performing a therapeutic procedure at the target location with the therapeutic device while a distal end of the sleeve catheter is proximally retracted to expose said device;

positioning the sleeve catheter to align an imaging device on the sleeve catheter at the target location; and imaging the target location with the imaging device.

6. A method as in claim 5, wherein the therapeutic procedure is performed prior to imaging the target location.

7. A method as in claim 6, wherein the therapeutic device is selected from the group consisting of a dilatation balloon, a cutting element, a laser, and an ultrasonic transducer and the first procedure comprises revascularization of a stenosed region in a blood vessel.

8. A method as in claim 5, wherein imaging the target location is performed prior to the therapeutic procedure.

9. A method as in claim 5, wherein the target location is imaged both before and after the therapeutic procedure.

10. A method as in claim 5, wherein the therapeutic catheter comprises a balloon catheter and the therapeutic procedure comprises angioplasty.

11. A method as in claim 5, wherein imaging comprises ultrasonic imaging.

12. An infusion catheter for use in combination with a base catheter, said infusion catheter comprising a sleeve having a tubular body with proximal and distal ends, an axial lumen in the tubular body which slidably receives the base catheter, and means within the distal end of the tubular body for infusing a therapeutic agent into adjacent diseased tissue.

13. An infusion catheter as in claim 12, wherein the infusing means comprises a plurality of infusion lumens disposed over a distal region of the sleeve catheter.

14. An infusion catheter as in claim 13, wherein the distal region of the sleeve is radially expandable, whereby the infusion lumens can be radially expanded by expanding a balloon within the lumen of the distal region of the sleeve catheter.

15. An infusion catheter as in claim 14, wherein the distal region of the sleeve is axially split to permit radial expansion.

16. An imaging catheter for use in combination with a base catheter, said imaging catheter comprising a sleeve having proximal and distal ends, an axial lumen having an open distal end which is adapted to removably receive the base catheter, and means at the distal end for imaging a surrounding region of a body lumen.

17. An imaging catheter as in claim 16, wherein the imaging means comprises an ultrasonic transducer array.

18. An imaging catheter as in claim 16, wherein the imaging means comprises an array of ultrasonic transducers disposed about the periphery of the distal end of the sleeve.

19. An imaging catheter as in claim 16, wherein the sleeve has at least one perfusion aperture disposed proximally of the imaging means, whereby perfusion flow can be established.

20. A method for delivering a therapeutic agent to a blood vessel in combination with another therapeutic procedure, said method comprising:
   introducing a base catheter comprising an angioplasty balloon at a distal end thereof and a sleeve catheter slidably disposed thereover to a stenotic region in the blood vessel;
   performing an angioplasty procedure at the stenotic region with the balloon while a distal end of the sleeve catheter is proximally retracted to expose said balloon;
   positioning a sleeve catheter to align an infusion matrix on the sleeve catheter for delivering the therapeutic agent at the stenotic region; and
   delivering therapeutic agent to said stenotic region through the infusion matrix on the sleeve catheter.

21. A method as in claim 20, wherein the sleeve catheter is aligned with the balloon of the balloon catheter within the stenotic region, further comprising inflating the balloon to contact the infusion matrix on the sleeve against the stenotic region, and delivering the therapeutic agent while contact is maintained between the infusion matrix and the stenotic region.

22. A method as in claim 20, wherein the infusion matrix on the sleeve catheter is aligned with the balloon on the base catheter and the therapeutic agent is delivered after performing the angioplasty procedure.

23. An infusion catheter for use in combination with a base catheter, said infusion catheter comprising a sleeve having proximal and distal ends, an axial lumen which slidably receives the base catheter, and means at the distal end thereof for infusing a therapeutic agent into adjacent diseased tissue, wherein the distal region of the sleeve is axially split to permit radial expansion.

24. An infusion catheter as in claim 23, wherein the infusing means comprises a plurality of infusion lumens disposed over a distal region of the sleeve catheter.

25. An infusion catheter as in claim 24, wherein the distal region of the sleeve is radially expandable, whereby the infusion lumens can be radially expanded by expanding a balloon within the lumen of the distal region of the sleeve catheter.

26. An imaging catheter for use in combination with a base catheter, said imaging catheter comprising a sleeve having proximal and distal ends, an axial lumen having an open distal end and a diameter in the range from 1.3 mm to 1.7 mm, and means at the distal end for imaging a surrounding region of a body lumen.

27. An imaging catheter as in claim 26, wherein the imaging means comprises an array of ultrasonic transducers disposed about the periphery of the distal end of the sleeve.

28. An imaging catheter as in claim 26, wherein the sleeve has at least one perfusion aperture disposed proximally of the ultrasonic transducer array, whereby perfusion flow can be established.

29. An imaging catheter for use in combination with a base catheter, said imaging catheter comprising a sleeve having proximal and distal ends, an axial lumen having an open distal end which is adapted to receive a base catheter selected from the group consisting of angioplasty catheters, atherectomy catheters, laser catheters, and stent delivery catheters, and means at the distal end for imaging a surrounding region of a body lumen.

30. An imaging catheter as in claim 29, wherein the imaging means comprises an array of ultrasonic transducers disposed about the periphery of the distal end of the sleeve.

31. An imaging catheter as in claim 29, wherein the sleeve has at least one perfusion aperture disposed proximally of the ultrasonic transducer array, whereby perfusion flow can be established.

* * * * *